(12) United States Patent
Patel

(10) Patent No.: US 7,153,834 B2
(45) Date of Patent: Dec. 26, 2006

(54) PHARMACEUTICAL COMPOSITIONS

(76) Inventor: Satishchandra P. Patel, 27 Yale St., Livingston, NJ (US) 07039

( * ) Notice: Subject to any disclaimer, the term of this patent is extended or adjusted under 35 U.S.C. 154(b) by 542 days.

(21) Appl. No.: 10/632,969

(22) Filed: Aug. 4, 2003

(65) Prior Publication Data

US 2004/0102366 A1  May 27, 2004

(30) Foreign Application Priority Data

Aug. 2, 2002 (GB) ................................. 0218003.2

(51) Int. Cl.
*A61K 38/13* (2006.01)
*C07K 7/64* (2006.01)

(52) U.S. Cl. ........................................ 514/15; 530/321

(58) Field of Classification Search ..................... None
See application file for complete search history.

(56) References Cited

U.S. PATENT DOCUMENTS

| | | | |
|---|---|---|---|
| 4,388,307 A | 6/1983 | Cavanak | |
| 5,342,625 A | 8/1994 | Hauer et al. | |
| 5,759,997 A | 6/1998 | Cavanak | |
| 5,858,401 A | 1/1999 | Bhalani et al. | |
| 6,057,289 A | 5/2000 | Mulye | |
| 6,248,363 B1 * | 6/2001 | Patel et al. ................. | 424/497 |
| 6,306,825 B1 | 10/2001 | Cavanak | |
| 2002/0009067 A1 | 1/2002 | Sachs et al. | |

FOREIGN PATENT DOCUMENTS

| | | |
|---|---|---|
| EP | 0 694 308 A1 | 1/1996 |
| EP | 0 813 876 A1 | 12/1997 |

* cited by examiner

*Primary Examiner*—Robert A. Wax
(74) *Attorney, Agent, or Firm*—Dickstein, Shapiro, LLP.

(57) ABSTRACT

Disclosed is a pharmaceutical composition suitable for oral administration in the form of a homogeneous solution which on exposure to water or gastrointestinal fluids forms an emulsion having a particle size of less than 5 microns, the solution containing:
(a) a pharmaceutically effective amount of a cyclosporin, in particular Cyclosporin A,
(b) a carrier medium which is a dialkyl ester of an aliphatic or aromatic dioic acid, the alkyl group of said dialkyl ester having from 2 to 8 carbon atoms, and said aliphatic or aromatic dioic acid having from 6 to 20 carbon atoms,
(c) a co-carrier having a hydrophilic lipophilic balance (HLB) of from 3 to 6, and
(d) a non-ionic surfactant having a hydrophilic lipophilic balance (HLB) greater than 10.

Examples of the carrier medium are dibutyl sebacate and dibutyl phthalate. Examples of the co-carrier are glycerol monooleate, sorbitan monooleate, glycerol monocaprylate, and sorbitan monolaurate.

22 Claims, No Drawings

PHARMACEUTICAL COMPOSITIONS

The present invention relates to pharmaceutical compositions, in particular a micro-emulsion concentrate for cyclosporins.

The cyclosporins are a class of cyclic undecapeptides, with important pharmacological activities, in particular immunosuppressive, anti-inflammatory and/or anti-parasitic activities. The first of the cyclosporins to be isolated, and the most commonly known cyclosporin, is Cyclosporin A, formulations of which are commercially available under the trade marks SANDIMMUNE and NEORAL The cyclosporins are very lipophilic and hydrophobic compounds, which are sparingly soluble in water, but dissolve readily in organic solvents such as methanol, ethanol, chloroform and the like. The low solubility in water results in extremely low bioavailability of the cyclosporins when administered orally. This may lead to higher dosages being required, with the consequent possibility of undesirable side effects. Therefore, to provide an effective therapeutic concentration of the drug in the body when administered orally represents a considerable challenge. Extensive research has been conducted to find cyclosporin formulations that are effective for oral administration. There are a number of preparations of cyclosporins suitable for oral administration proposed by the prior art.

Prior art formulations of cyclosporins for oral administration have often involved combinations of the cyclosporin with a surfactant, an oil, and a co-surfactant. Such formulations have been intended to be diluted with water prior to drinking. However, this is rather inconvenient, and also the resulting aqueous composition has an unpleasant taste.

In order to alleviate the problems of having to dilute the composition with water prior to oral administration, and the unpleasant taste of the resulting solution, liquid compositions have been formulated into soft capsule preparations. For example, the formulation commercially available under the trade mark SANDIMMUNE is encapsulated in a soft capsule with a gelatine shell. The formulation contains ethanol in order to solubilise the cyclosporin. However, the ethanol can permeate the gelatine shell of the capsule and is volatile at room temperature. This means that the composition of the contents can vary during storage. If too much ethanol is lost, the cyclosporin may precipitate from the composition, with adverse effects on the bioavailability. This results in uncertainties about dosage.

U.S. Pat. No. 4,388,307 discloses compositions comprising a cyclosporin together with at least one of the following components:
  a) a trans-esterification product of a natural or hydrogenated vegetable oil triglyceride and a polyalkylene polyol;
  b) a saturated fatty acid triglyceride; and
  c) a mono- or di-glyceride.

It is preferred that ethanol be used as a further solubilising agent, and the compositions for oral administration disclosed in the Examples all contain ethanol.

U.S. Pat. No. 5,342,625 discloses pharmaceutical compositions comprising cyclosporins in micro-emulsion pre-concentrate and micro-emulsion form. The compositions contain a cyclosporin disposed in a composition comprising a hydrophilic phase, a lipophilic phase and a surfactant. The hydrophilic phase comprises 1,2-propylene glycol or $R_1$—(O—($CH_2$))$_x$—$OR_2$ wherein $R_1$ is a $C_{1-5}$ alkyl or a tetrahydrofurfuryl group, $R_2$ is a $C_{1-5}$ alkyl or a tetrahydrofurfuryl group or is hydrogen, and X is from 1 to 6. The lipophilic phase typically comprises a fatty acid triglyceride. The compositions may contain a $C_{1-5}$ alkanol, such as ethanol, as a co-solvent. However, the compositions disclosed in U.S. Pat. No. 5,342,625 include components which are restricted for pharmaceutical use by several regulatory agencies world-wide, including the FDA, because they are not considered "Generally Recognised As Safe" (GRAS) for oral use.

U.S. Pat. No. 5,759,997 discloses pharmaceutical compositions comprising a cyclosporin, a fatty acid triglyceride, and a glycerol fatty acid partial ester or propylene glycol or sorbitol complete or partial ester. The compositions may also comprise a viscosity reducer, such as the trans-esterification product of a natural vegetable oil triglyceride and a polyalkylene polyol. Ethanol can also be used, but is less preferred. The compositions may also comprise an emulsifying agent, preferably a tenside having a hydrophilic-lipophilic balance (HLB) of at least 10.

U.S. Pat. No. 6,057,289 discloses pharmaceutical compositions comprising cyclosporin and a carrier comprising
  (a) a cyclosporin solubilising agent consisting essentially of $C_6$ to $C_{22}$ fatty acids; and
  (b) a water-soluble non-ionic surfactant.

The surfactant should have a hydrophilic-lipophilic balance (HLB) greater than 10, and suitable surfactants include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like. The compositions are for forming microemulsions upon contact with an aqueous medium.

U.S. Pat. No. 5,858,401 discloses compositions that comprise a cyclosporin, a medium chain monoglyceride of $C_6$ to $C_{12}$ fatty acids, having a monoglyceride content of at least 50%, and at least one surfactant. The surfactant may be, for example, polyglycolised glycerides or ethoxylated glycerides having a molecular weight of PEG between 400 and 2000 and a fatty acid chain length between $C_6$ to $C_{18}$. The compositions are for forming microemulsions upon contact with an aqueous medium.

Having regard to the state of the art, it is clear that it is desirable to provide further formulations of cyclosporins suitable for oral administration, and in particular ones which can be formulated in capsules such as soft gelatine capsules, and which are emulsion concentrates (that is, homogeneous solutions which on exposure to water or gastrointestinal fluids form an emulsion having a particle size of less than 5 microns), and preferably microemulsion concentrates, which avoid the use of volatile components such as ethanol, and which utilise compounds which are Generally Recognised As Safe (GRAS).

There is also a continued need to provide cyclosporin formulations for oral administration which can have high cyclosporin concentrations (thereby reducing the size of capsule required for a given dosage), which exhibit high oral bioavailability, and which are stable (in particular stable against precipitation of the cyclosporin) upon storage. It is also desirable that formulations should have as few components as possible, thereby resulting in ease of manufacture.

The present invention aims to provide cyclosporin compositions which, at least to some extent, satisfy these requirements.

According to the present invention, there is provided a pharmaceutical composition suitable for oral administration in the form of a homogeneous solution which on exposure to water or gastrointestinal fluids forms an emulsion having a particle size of less than 5 microns, the solution comprising:

(a) a pharmaceutically effective amount of a cyclosporin,
(b) a carrier medium comprising a dialkyl ester of an aliphatic or aromatic dioic acid, the alkyl group of said dialkyl ester having from 2 to 8 carbon atoms, and said aliphatic or aromatic dioic acid having from 6 to 20 carbon atoms,
(c) a co-carrier having a hydrophilic lipophilic balance (HLB) of from 3 to 6, and
(d) a non-ionic surfactant having a hydrophilic lipophilic balance (HLB) greater than 10.

The present invention is partly based upon the discovery that the carrier medium as defined in (b) above represents a particularly good solvent medium for cyclosporins, and therefore it is possible to avoid co-solvents such as ethanol, propylene glycol, or the like. The compositions according to the present invention accordingly preferably do not have such co-solvents, and in particular preferably do not contain ethanol.

The compositions according to the present invention preferably do not contain appreciable amounts of water, that is, they are substantially water-free.

The compositions according to the present invention exhibit excellent stability upon storage, and high concentrations of cyclosporins in the compositions can be achieved.

The compositions according to the present invention are homogeneous mixtures which exhibit excellent bioavailability of the cyclosporin in vivo.

The cyclosporin is preferably Cyclosporin A. The cyclosporin preferably makes up from 1 to 25% by weight of the composition, more preferably makes up from 5 to 20% by weight of the composition, and most preferably makes up from 10 to 20% by weight of the composition. The cyclosporin is present in the composition of the present invention in pharmaceutically effective amounts. These amounts are well-known in the art. For example, when treating chronic inflammations or provoking an immunosuppressive effect, it is preferred that the daily dose ranges from about 3 mg/kg to about 50 mg/kg.

The carrier medium may comprise a dialkyl ester of an aliphatic or of an aromatic acid. When the acid is an aliphatic acid, the acid preferably has from 8 to 12 carbon atoms, and more preferably has 10 carbon atoms. Most preferably, the aliphatic acid is sebacic acid. When the acid is an aromatic acid, the acid preferably has from 6 to 10 carbon atoms, and more preferably has 8 carbon atoms. Most preferably, the aromatic acid is phthalic acid. Each alkyl group of the dialkyl ester (which may be the same or different, but is preferably the same) has from 2 to 8 carbon atoms, preferably has from 3 to 6 carbon atoms, more preferably has 4 carbon atoms, and most preferably is an n-butyl group.

Thus, the most preferred compounds for the carrier medium are dibutyl phthalate and dibutyl sebacate.

The carrier medium may comprise mixtures of compounds as defined herein.

The carrier medium preferably makes up from 20 to 60% by weight of the composition, more preferably makes up from 25 to 50% by weight of the composition, and most preferably makes up from 30 to 40% by weight of the composition.

The non-ionic surfactant preferably makes up from 5 to 40% by weight of the composition, more preferably makes up from 10 to 35% by weight of the composition, and most preferably makes up from 15 to 25% by weight of the composition.

The Hydrophilic Lipophilic Balance (HLB) of the non-ionic surfactant is greater than 10, more preferably greater than 12 and most preferably greater than 14.

The non-ionic surfactant must be capable of forming a stable emulsion, preferably a fine emulsion (particle size less than 1 micron), and more preferably a microemulsion, of the composition when it is brought into contact with aqueous fluid, such as in the G.I. tract.

The non-ionic surfactant is preferably selected from the group consisting of: polyoxyethylene products of hydrogenated vegetable oils, polyethoxylated castor oils, polyethoxylated hydrogenated castor oil, polyoxyethylene-sorbitan-fatty acid esters, and polyoxyethylene castor oil derivatives. Particularly preferred surfactants are set out in Table 1. Mixtures of these surfactants can also be used.

TABLE 1

| Trade Name | Description |
| --- | --- |
| TWEEN 20 | Polyoxyethylene (20) sorbitan monolaurate |
| TWEEN 40 | Polyoxyethylene (20) sorbitan monopalmitate |
| TWEEN 60 | Polyoxyethylene (20) sorbitan monostearate |
| TWEEN 80 | Polyoxyethylene (20) sorbitan monooleate |
| NIKKOL HCO30 | PEG-30 hydrogenated castor oil |
| NIKKOL HCO40 | PEG-40 hydrogenated castor oil |
| NIKKOL HCO50 | PEG-50 hydrogenated castor oil |
| NIKKOL HCO60 | PEG-60 hydrogenated castor oil |
| CREMOPHORE RH40 | Polyoxyethylene 40 castor oil |
| CREMOPHORE RH60 | Polyoxyethylene 60 castor oil |
| CREMOPHORE EL35 | Polyoxyethylene 35 castor oil |

The co-carrier is added to form an isotropic mixture. The co-carrier preferably makes up from 25 to 50% by weight of the composition, and more preferably from 30 to 40% by weight of the composition.

The co-carrier has an HLB value of from 3 to 6, and any such co-carrier that is safe for oral administration is suitable. The co-carrier is preferably a monoester of glycerol or sorbitan with an aliphatic monocarboxylic acid having from 6 to 30 carbon atoms. Preferably, the aliphatic monocarboxylic acid has from 8 to 18 carbon atoms. Particularly preferred co-carriers are glycerol monooleate, glycerol monocaprylate, sorbitan monooleate, and sorbitan monolaurate, and mixtures thereof Such suitable co-carriers are commercially available.

The pharmaceutical compositions according to the present invention may further comprise an antioxidant. This antioxidant, when present, is preferably present in an amount of from 0.01% to 2% by weight of the composition, and more preferably from 0.5 to 1% by weight of the composition. The antioxidant may be any suitable antioxidant, such as are well known to those skilled in the art. Particularly preferred antioxidants are butyl hydroxy anisole (BHA), butyl hydroxy toluene (BHT), and alpha-tocopherol.

Other additives, excipients, and diluents normally used in the pharmaceutical arts may optionally be added to the composition. These include thickening agents, dispersing agents, flavouring agents, sweetening agents, colouring agents, stabilising agents (including pH stabilisers), and preservatives. However, the compositions of the present invention preferably consist only of the components defined in claim 1, or at least comprise at least 90%, more preferably at least 95%, and more preferably at least 98% by weight of the components defined in claim 1.

The pharmaceutical compositions according to the present invention may be formulated as a drinking solution, or as a hard or soft capsule. Soft capsule formulations are particularly preferred. Gelatine capsules are also preferred.

The pharmaceutical compositions according to the present invention can be conveniently prepared by uniformly and thoroughly mixing the carrier medium, the cyclosporin, and the surfactant together at room temperature or at slightly elevated temperature, such as a temperature up to 40° C., until a clear solution is obtained, and then cooling the composition to room temperature. The other additives indicated above are then thoroughly admixed therewith. The cyclosporin remains in solution and does not crystallise or precipitate out.

Compositions according to the present invention are preferably for administration to mammals, and especially to humans. It is preferred that the pharmaceutical compositions of the present invention are administered in capsule, liquid-oral, drink solution, or the like form. In a preferred embodiment, the composition is in a form adapted for oral administration in oral unit dosage form. Capsules, e.g., soft or hard gelatine capsules, which represent the preferred oral dosage form, are specially suitable unit dosage forms for oral administration.

Oral unit dosage forms in accordance with the present invention will suitably comprise from 5 to 400 mg and more preferably from 20 to 200 mg, e.g., 25, 50, 100, 125, 150, or 200 mg of cyclosporin. The dosage of the drug and the number of times administered to the patient will vary depending on several factors such as: the age of the patient, the severity of the condition of the patient, and past medical history, and will be a matter to be determined by the attending physician.

When the composition of the present invention is prepared in the form of a soft or hard capsule, the composition may be encapsulated in a gelatine shell which contains any conventional plasticizer. Suitable plasticizers are: glycerine, sorbitol, hexanetriol propylene carbonate, hexane glycol, sorbitans, tetrahydrofuryl alcohol ether, diethylene glycol monoethyl ether, 1,3-trimethyl-2-imidazolidone, dimethylisosorbide, and mixtures of these. However, the plasticizer is not limited to those just mentioned, and any suitable plasticizer can be used.

Encapsulation can be achieved by standard techniques which are well known in the art.

Compositions according to the present invention exhibit high solubility of cyclosporin, thereby reducing the size of the capsule or other oral unit dosage form. They also employ only materials that are GRAS for oral use.

The invention will now be further described with reference to the following Examples, it being understood that these are intended to illustrate the invention, and in no way to limit its scope.

EXAMPLES

The examples used the ingredients and in the amounts indicated in Table 2. Cyclosporin A was dissolved in the carrier medium, the other components were added, and the mixture was mixed for from 10 to 30 minutes at room temperature until the solution was homogeneous.

The solution was then stored overnight up to 24 hours to ensure that no crystallisation occurred.

To verify that an emulsion was formed, one part of each composition was added to 10 parts of water and stirred gently. There was formed a fine emulsion having a particle size of less than 5 microns, and the Cyclosporin A did not precipitate or crystallise out.

The compositions are suitable for encapsulation into a hard or soft gelatine capsule.

TABLE 2

| Ingredients | Example 1 weight/mg | Example 2 weight/mg | Example 3 weight/mg |
|---|---|---|---|
| Cyclosporin A | 100 | 100 | 100 |
| Dibutyl sebacate | 220 | 220 | 220 |
| Glycerol mono oleate | 220 | | |
| Glycerol mono caprylate | | 220 | |
| Sorbitan mono oleate | | | 220 |
| Polyoxyethylene 35 castor oil (cremophore EL) | 150 | 150 | 150 |
| Alpha tocopherol | 5 | 5 | 5 |
| TOTAL | 695 mg | 695 mg | 695 mg |

Thus, it can be seen that the compositions of the present invention allow high concentrations of cyclosporins to be obtained, which exhibit good stability on storage. The compositions of the present invention allow higher concentrations of cyclosporin to be obtained than current commercial preparations (Sandimune, Neoral).

The invention claimed is:

1. A pharmaceutical composition suitable for oral administration in the form of a homogeneous solution which on exposure to water or gastrointestinal fluids forms an emulsion having a particle size of less than 5 microns, the solution comprising:
    (a) a pharmaceutically effective amount of a cyclosporin,
    (b) a carrier medium comprising a dialkyl ester of an aliphatic or aromatic dioic acid, the alkyl group of said dialkyl ester having from 2 to 8 carbon atoms, and said aliphatic or aromatic dioic acid having from 6 to 20 carbon atoms,
    (c) a co-carrier having a hydrophilic lipophilic balance (HLB) of from 3 to 6, and
    (d) a non-ionic surfactant having a hydrophilic lipophilic balance (HLB) greater than 10.

2. A pharmaceutical composition according to claim 1 wherein the carrier medium comprises a di-$C_{3-6}$-alkyl ester of a $C_{8-12}$-aliphatic dioic acid or $C_{6-10}$-aromatic dioic acid.

3. A pharmaceutical composition according to claim 1 wherein the carrier medium comprises a di-$C_4$-alkyl ester of a $C_{10}$-aliphatic dioic acid or C8-aromatic dioic acid.

4. A pharmaceutical composition according to claim 1 wherein the carrier medium comprises a dibutyl ester of an aliphatic or aromatic dioic acid.

5. A pharmaceutical composition according to claim 4, wherein the carrier medium comprises dibutyl sebacate or dibutyl phthalate.

6. A pharmaceutical composition according to claim 1, wherein the cyclosporin is 1 to 25% by weight of the composition, the carrier medium is 20 to 60% by weight of the composition, the non-ionic surfactant is 15 to 25% by weight of the composition, and the co-carrier is 25 to 50% by weight of the composition.

7. A pharmaceutical composition according to claim 6, wherein the cyclosporin is 5 to 20% by weight of the composition, the carrier medium is 25 to 50% by weight of the composition, and the non-ionic surfactant is 10 to 35% by weight of the composition.

8. A pharmaceutical composition according to claim 7, wherein the cyclosporin is 10 to 20% by weight of the composition, the carrier medium is 30 to 40% by weight of the composition, the non-ionic surfactant is 15 to 25% by weight of the composition, and the co-carrier is 30 to 40% by weight of the composition.

9. A pharmaceutical composition according to claim 1, wherein the non-ionic surfactant is selected from the group consisting of: polyoxyethylated hydrogenated vegetable oil, polyethoxylated castor oil, polyethoxylated hydrogenated castor oil, polyoxyethylene-sorbitan-fatty acid ester, polyoxyethylene castor oil derivative, and mixtures thereof.

10. A pharmaceutical composition according to claim 9, wherein the non-ionic surfactant is selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan monooleate, PEG-30 hydrogenated castor oil, PEG-40 hydrogenated castor oil, PEG-50 hydrogenated castor oil, PEG-60 hydrogenated castor oil, polyoxyethylene (40) castor oil, polyoxyethylene (60) castor oil, polyoxyethylene (35) castor oil, and mixtures thereof.

11. A pharmaceutical composition according to claim 1, wherein the co-carrier is selected from the group consisting of monoesters of glycerol or sorbitan with an aliphatic monocarboxylic acid having from 6 to 30 carbon atoms, preferably from 8 to 18 carbon atoms, and mixtures thereof.

12. A pharmaceutical composition according to claim 11, wherein the co-carrier is selected from the group consisting of monoesters of glycerol or sorbitan with an aliphatic monocarboxylic acid having from 8 to 18 carbon atoms and mixtures thereof.

13. A pharmaceutical composition according to claim 12, wherein the co-carrier is selected from the group consisting of glycerol monooleate, sorbitan monooleate, glycerol monocaprylate, sorbitan monolaurate, and mixtures thereof.

14. A pharmaceutical composition according to claim 1, further comprising an antioxidant.

15. A pharmaceutical composition according to claim 14, wherein the antioxidant is present in an amount of from 0.01% to 2% by weight of the total composition.

16. A pharmaceutical composition according to claim 14, wherein the antioxidant is selected from the group consisting of BHA, BHT, and alpha-tocopherol.

17. A pharmaceutical composition according to claim 1, wherein the cyclosporin is Cyclosporin A.

18. A pharmaceutical composition according to claim 1, wherein the cyclosporin is 1 to 25% by weight of the composition, the carrier medium is 20 to 60% by weight of the composition and comprises a di-$C_{3-6}$-alkyl ester of a $C_{8-12}$-aliphatic dioic acid or $C_{6-10}$-aromatic dioic acid, the non-ionic surfactant is 15 to 25% by weight of the composition and has an HLB greater than 10, the co-carrier is 25 to 50% by weight of the composition, and the composition contains from 0.01% to 2 % by weight of an antioxidant.

19. A pharmaceutical composition according to claim 18, wherein the cyclosporin is 10 to 20% by weight of the composition and comprises Cyclosporin A, the carrier medium is 30 to 40% by weight of the composition and comprises dibutyl sebacate or dibutyl phthalate, the non-ionic surfactant is 15 to 25% by weight of the composition and has a HLB greater than 14, the co-carrier is 30 to 40% by weight of the composition and the composition contains from 0.5% to 21% by weight of an antioxidant selected from the group consisting of BHA, BHT, and alpha-tocopherol.

20. A pharmaceutical composition according to claim 1, formulated as a drinking solution.

21. A pharmaceutical composition according to claim 1 formulated as a hard or soft capsule.

22. A pharmaceutical composition according to claim 19 contained within a soft gelatine capsule.

\* \* \* \* \*